(12) United States Patent
Cembrowski et al.

(10) Patent No.: US 10,332,621 B2
(45) Date of Patent: *Jun. 25, 2019

(54) METHOD AND APPARATUS FOR CALIBRATION AND TESTING OF SCIENTIFIC MEASUREMENT EQUIPMENT

(71) Applicant: George S. Cembrowski, Edmonton (CA)

(72) Inventors: George S. Cembrowski, Edmonton (CA); David Vu Tran, Edmonton (CA)

(73) Assignee: CCQCC CORP., Alberta (CA)

( * ) Notice: Subject to any disclaimer, the term of this patent is extended or adjusted under 35 U.S.C. 154(b) by 199 days.

This patent is subject to a terminal disclaimer.

(21) Appl. No.: 14/027,463

(22) Filed: Sep. 16, 2013

(65) Prior Publication Data
US 2014/0172311 A1    Jun. 19, 2014

Related U.S. Application Data

(63) Continuation of application No. 12/841,055, filed on Jul. 21, 2010, now Pat. No. 8,538,727.
(Continued)

(51) Int. Cl.
*G01N 35/00* (2006.01)
*G16H 10/60* (2018.01)

(52) U.S. Cl.
CPC ....... *G16H 10/60* (2018.01); *G01N 35/00613* (2013.01); *G01N 2035/0094* (2013.01); *G01N 2035/00653* (2013.01)

(58) Field of Classification Search
CPC . G01N 2035/00653; G01N 2035/0094; G01N 35/00613; G01N 2001/2893
(Continued)

(56) References Cited

U.S. PATENT DOCUMENTS 4,202,033 A * 5/1980 Strobel .................. 436/183
4,627,014 A * 12/1986 Lo et al. ................. 702/25
(Continued)

OTHER PUBLICATIONS

"U.S. Appl. No. 12/841,055, Response filed Oct. 15, 2012 to Non Final Office Action dated Apr. 13, 2012", 9 pgs.
(Continued)

*Primary Examiner* — Manuel L Barbee
*Assistant Examiner* — Raymond L Nimox
(74) *Attorney, Agent, or Firm* — Schwegman Lundberg & Woessner, P.A.

(57) ABSTRACT

Discussed herein are methods and apparatuses to produce profiles for scientific measurement equipment, and to use those profiles for various purposes in using, designing, calibrating and managing such equipment, such as to carry out critical laboratory testing. In this approach, either the analyzers' quality control data or serial patient data are numerically reduced to generate graphical precision profiles. Precision profiles for serial patient data show increased (im)precision vs time implying increased patient variation over increased time. Precision profiles for quality control data, according to one implementation, can demonstrate three different zones: 1) increased imprecision for quality control determinations that are close spaced (implies the discovery of an error condition and rapid reanalysis, 2) the usual imprecision and 3) a zone of increased imprecision which indicates either a need for a quality control analysis or re-calibration.

19 Claims, 10 Drawing Sheets

Related U.S. Application Data

(60) Provisional application No. 61/227,348, filed on Jul. 21, 2009.

(58) Field of Classification Search
USPC .......................................................... 702/85
See application file for complete search history.

(56) References Cited

U.S. PATENT DOCUMENTS

| | | | |
|---|---|---|---|
| 4,858,154 | A | 8/1989 | Anderson et al. |
| 5,210,778 | A | 5/1993 | Massart |
| 5,360,613 | A * | 11/1994 | Nissen .......................... 424/439 |
| 5,541,854 | A * | 7/1996 | Yundt ............................ 702/19 |
| 6,157,041 | A | 12/2000 | Thomas et al. |
| 6,787,361 | B1 * | 9/2004 | Klee ....................... G01N 33/50 436/43 |
| 8,538,727 | B2 * | 9/2013 | Cembrowski .... G01N 35/00613 702/179 |
| 2003/0083901 | A1 * | 5/2003 | Bosch et al. ........................ 705/2 |
| 2003/0101012 | A1 * | 5/2003 | Parvin .............. G01N 35/00594 702/84 |
| 2004/0078162 | A1 | 4/2004 | Yundt-pacheco |
| 2007/0198213 | A1 * | 8/2007 | Parvin ................... G06F 19/366 702/179 |
| 2008/0186133 | A1 * | 8/2008 | Parkhurst ......... G01N 35/00613 340/5.8 |
| 2009/0287356 | A1 | 11/2009 | Dunne |
| 2011/0022343 | A1 | 1/2011 | Cembrowski |
| 2011/0111439 | A1 | 5/2011 | Hecker et al. |

OTHER PUBLICATIONS

"U.S. Appl. No. 12/841,055, Non Final Office Action dated Apr. 13, 2012", 13 pgs.

"U.S. Appl. No. 12/841,055, Notice of Allowance dated May 20, 2013", 12 pgs.

"U.S. Appl. No. 12/841,055, Response filed Feb. 21, 2013 to Restriction Requirement dated Jan. 25, 2013", 79 pgs.

"U.S. Appl. No. 12/841,055, Response filed May 6, 2013 to Restriction Requirement dated Jan. 25, 2013", 80 pgs.

"U.S. Appl. No. 12/841,055, Restriction Requirement dated Jan. 25, 2013", 5 pgs.

"U.S. Appl. No. 12/841,055, Supplemental Amendment filed May 9, 2013", 11 pgs.

"U.S. Appl. No. 12/841,055, Supplemental Notice of Allowability dated Jul. 25, 2013", 6 pgs.

Cembrowski, G. S., et al., "The use of serial patient blood gas, electrolyte and glucose results to derive biologic variation: a new tool to assess the acceptability of intensive care unit testing", Clin. Chem. Lab. Med., 48(10), (2010), 1447-1454.

Tran, D. V., et al., "Unique Approach to Derivation of Random Error in Laboratory Assays: Application to Glycohemoglobin Testing Demonstrates Poor Clinical Performance for Immunochemistry Assay", Diabetes Technology & Therapeutics, 5(6), (2003), 975-978.

Tran, D. V., et al., "Use of 2 years of patient data to estimate intra-laboratory total imprecision of HbA(1c) measured by multiple HPLC analyzers", Clinical Biochemistry, 41, (2008), 177-179.

* cited by examiner

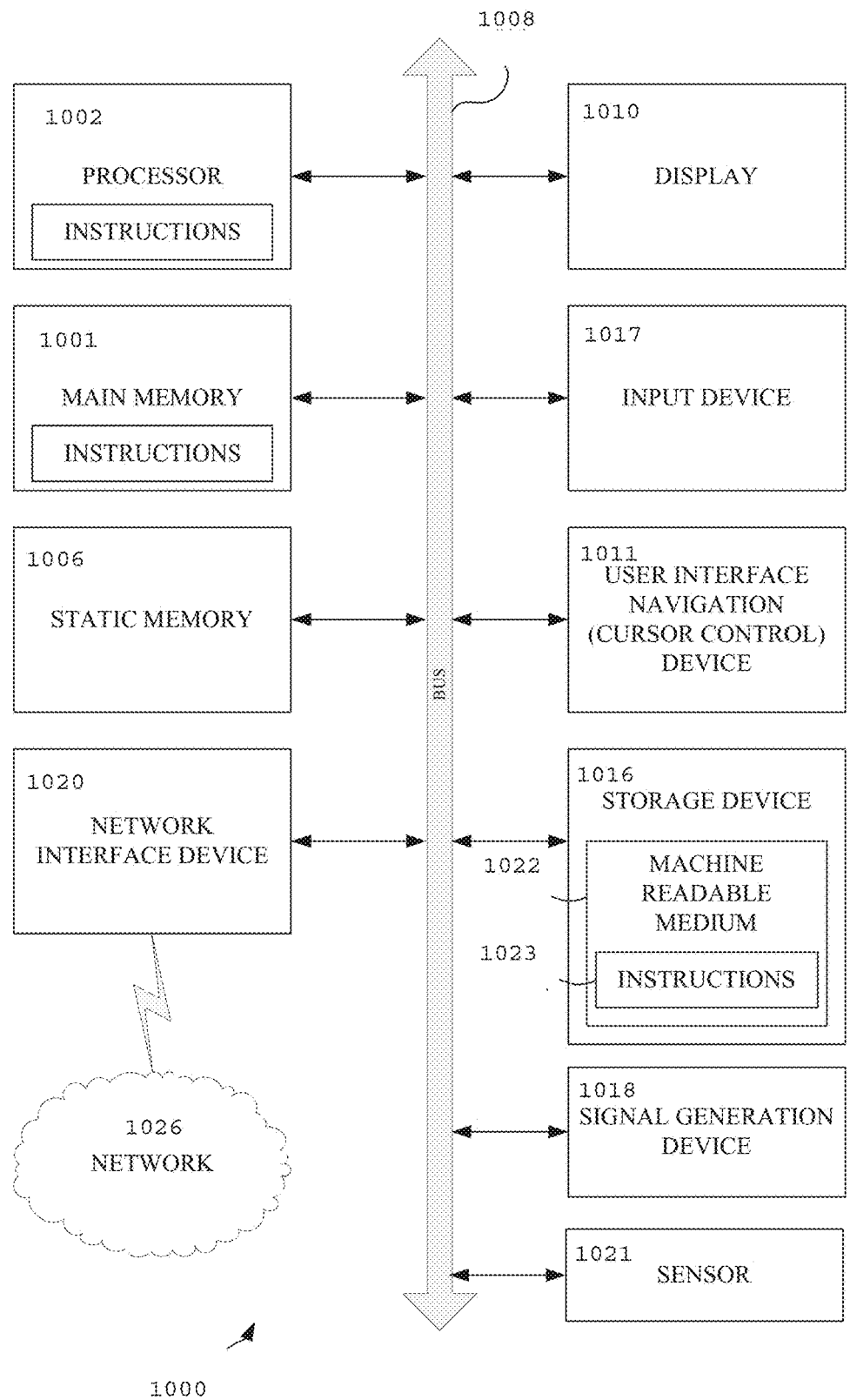

METHOD AND APPARATUS FOR CALIBRATION AND TESTING OF SCIENTIFIC MEASUREMENT EQUIPMENT

PRIORITY APPLICATION(S)

This patent application is a continuation of and claims the benefit of priority to U.S. patent application Ser. No. 12/841,055, filed Jul. 21, 2010, which claims the benefit of priority, under 35 U.S.C. § 119(e), to U.S. Provisional Patent Application Ser. No. 61/227,348, filed Jul. 21, 2009, the benefit of priority of each of which is claimed hereby, and each of which are incorporated herein by reference in its entirety.

TECHNICAL FIELD

The inventive subject matter relates generally to scientific measurement equipment and devices, and more particularly to method and apparatus for testing, comparing and calibrating scientific measurement equipment and devices.

BRIEF DESCRIPTION OF DRAWINGS

FIG. 10 illustrates a computer system.

DETAILED DESCRIPTION

Clinical laboratory analyzers are used extensively in the medical and forensics profession and in research to perform tests on biological and other substances. The proper calibration and operation of these analyzers, and other laboratory equipment, is critical to producing accurate test results for patients and accurate measurements for researchers. As a result, proper use of such equipment requires regular recalibration. Such recalibration may be performed on a periodic basis based on the passage of time, or may be based on the number of uses of equipment between calibration, or based on a test of the equipment to determine its accuracy and recalibration only as necessary to maintain the desired accuracy level.

According to one example embodiment, there is described method, and apparatus, including programmed computers, to produce precision profiles for scientific measurement equipment in general, and in particular clinical laboratory analyzers. In this approach, either the analyzers' quality control data or serial patient data are numerically reduced to generate graphical precision profiles. Precision profiles for serial patient data show increased (im)precision vs time implying increased patient variation over increased time. Precision profiles for quality control data, according to one implementation, can demonstrate three different zones: 1) increased imprecision for quality control determinations that are close spaced (implies the discovery of an error condition and rapid reanalysis, 2) the usual imprecision and 3) a zone of increased imprecision which indicates either a need for a quality control analysis or re-calibration.

These precision profiles are used to summarize and compare the performance of the different analyzers that have produced these quality control or patient data. These precision profiles are also used to improve the quality control practices that are used with the analyzers.

To generate the quality control precision profile, on approach is to statistically summarize all of the quality control data that are generated for a particular test and quality control level (all of the qc data generated from the analysis of a one or more lots of quality control material of a single level over a period of several weeks to several years). To generate the patient data precision profile, one approach is to statistically reduce large volumes (at least 3 months) of patient data that are produced by hospital clinical laboratory analyzers, including point of care analytic systems.

Figure 1:
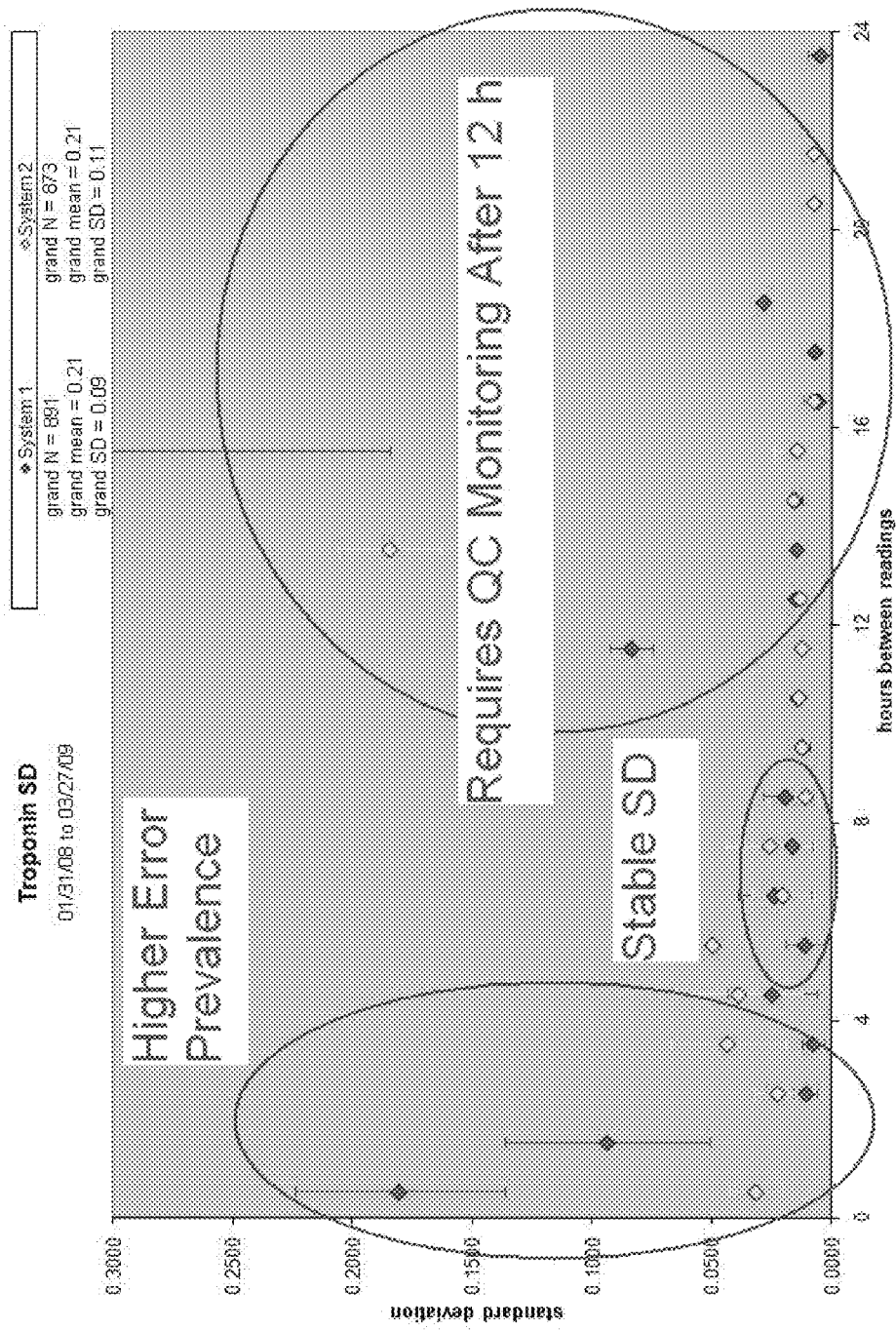
FIG. 1 shows a representative 24 hour precision profile graph for quality control data.
Figure 2:
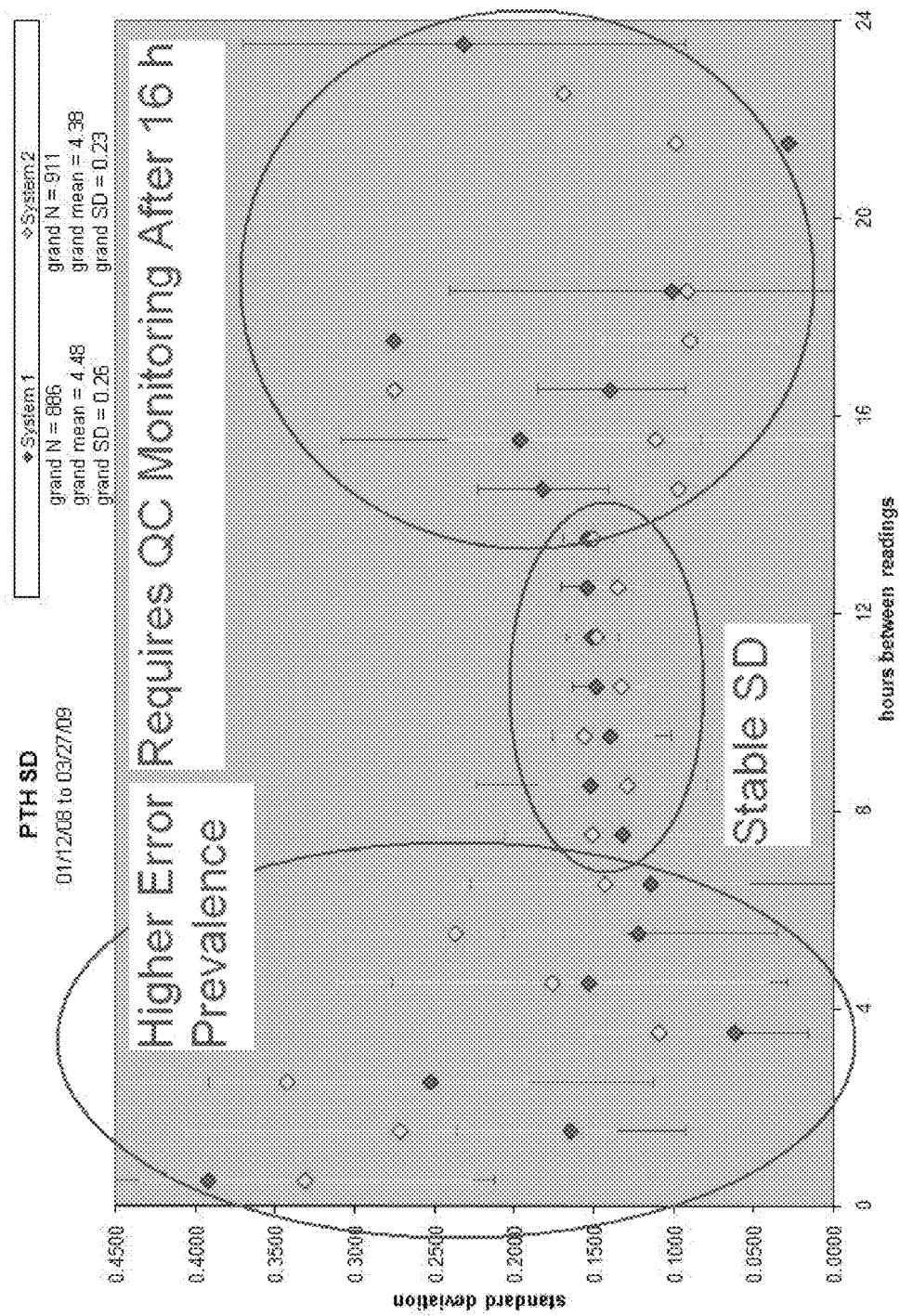
FIG. 2 shows a representative quality control precision profile graph.
Figure 3:
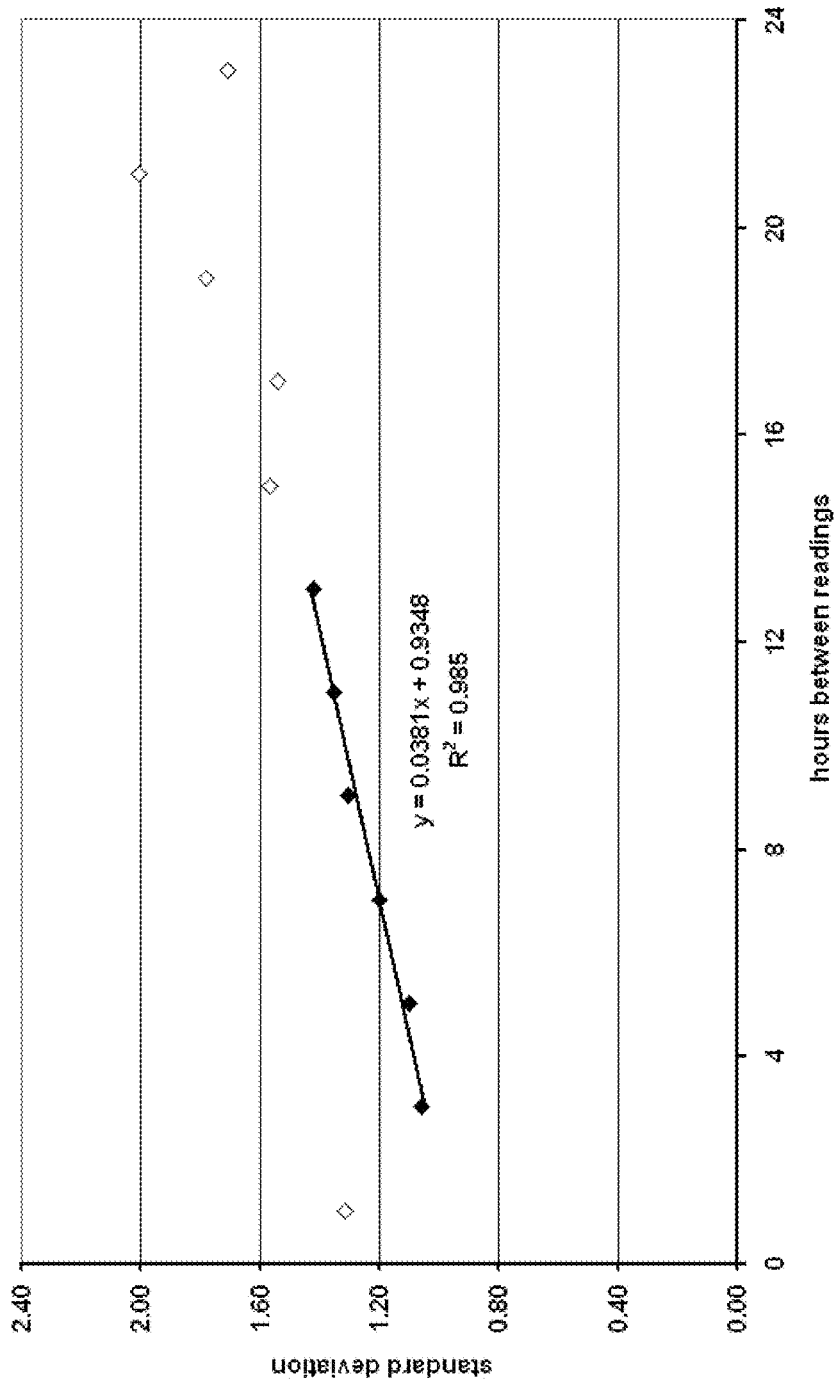
FIG. 3 shows a patient precision profile graph for sodium analyzed in an intensive care unit.

FIG. 1 is a graph showing a representative 24 hour precision profile for quality control data for the troponin (used to diagnose myocardial infarction) test and FIG. 2 is a graph showing a representative quality control precision profile for the PTH (parathyroid hormone) test. FIG. 3 is a graph showing a patient precision profile for sodium analyzed in an intensive care unit. These error vs. time profiles can be used to summarize and compare the analytic precision and indirectly the accuracy of different analytic technologies in the clinical laboratory.

According to one example embodiment, a precision profile may be used for quality control as follows:

Determine the optimal quality control limits for the application of statistical quality control of the laboratory analyzer Demonstrate outlying quality control data Demonstrate the general times that analytic errors may be more prevalent Demonstrate when quality control specimens should be analyzed Compare analytic precision of similar systems in similar or different laboratory environments [referral laboratory, university hospital laboratory, near patient testing (point of care)].

Use to educate laboratorian on appropriate quality control practices

Use all the above to classify analyzers as in or out of compliance with quality control requirements and to determine how and when to calibrate the analyzers (measurement equipment in general)

According to another example embodiment, a precision profile may be used to provide a patient data precision profile as follows:

Evaluate total analytic imprecision starting from blood drawing, to specimen processing to analysis and reporting Recommend how to use clusters of analyzers in the most appropriate manner (for example, if a laboratory has two systems, should it be using one system for a week or a month and not run the other or should there be alternation between the two systems, and what would be the most favorable period that each would be run before alternating to the other system)

Help determine whether change of calibration frequency will improve quality of analytic results Compare analytic precision of different systems in different laboratory environments (referral laboratory, university hospital laboratory, near patient testing (point of care).

The process and compute programs for the data analysis which provides these profiles for both patient and quality control data is described in more detail in the attached paper: *The Use of Serial Patient Blood Gas Electrolyte and Glucose Results to Derive Biologic Variation*, the entirety of which is hereby incorporated herein by reference. This paper describes the analysis of patient data. Quality control data can be reduced in the same manner with one level of quality control representing one patient who is measured over the time of viability of the quality control product. Also attached and incorporated by reference are four studies: *Use of Patient Result-Derived Imprecisions to Assess the Analytic Quality of Electrolyte and Creatinine Measurements* by Vitros and Beckman *Methodologies, The Use of Serial Patient Blood Gas, Electrolyte and Glucose Results to Derive Biologic Variation: a New Tool to Gauge the Acceptability of ICU Testing, Use of Serial Patient Differences of HPLC HbA1c to Determine Long Term Instrument Performance*, and Tandem Roche Hitachi 917, and Tandem Beckman LX-20 Operated in Two Tertiary Care Hospitals Exhibit Comparable Total Patient-Based Imprecisions.

Figure 4:
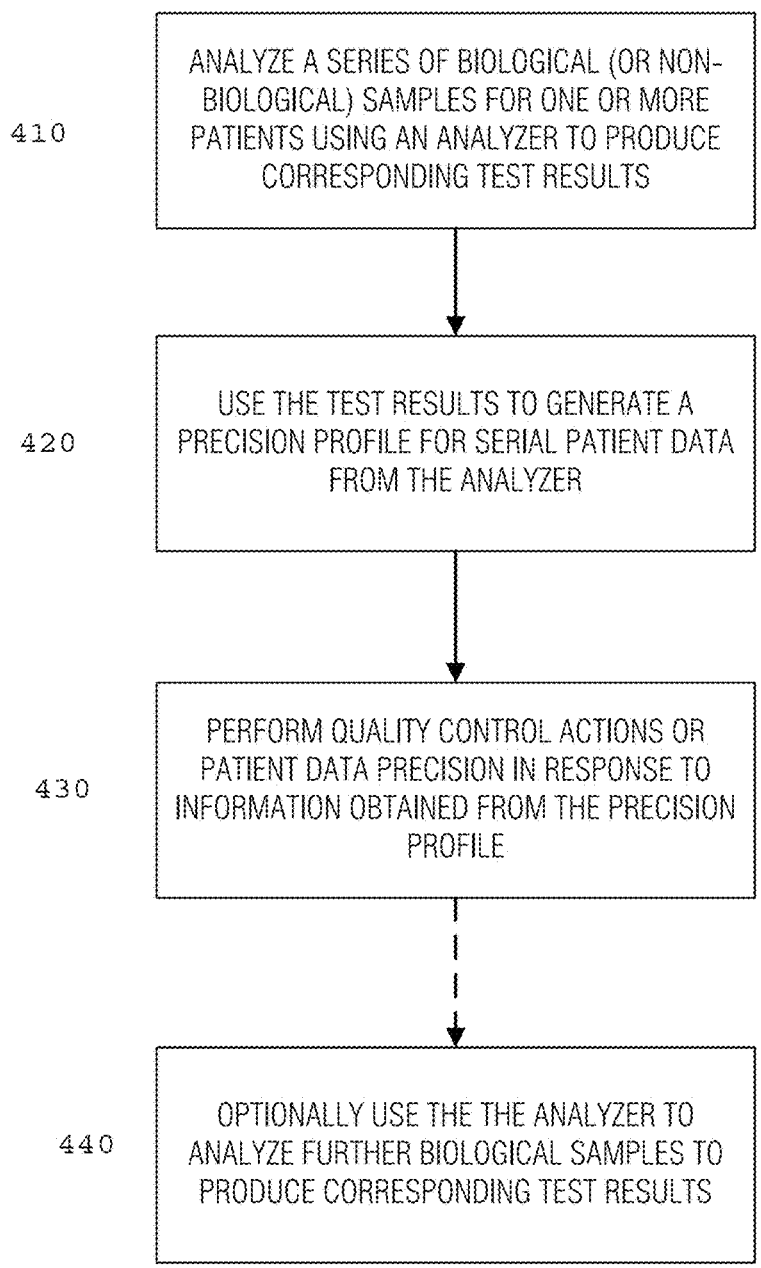
FIGS. 4 through 8 illustrate various methods and computer programs according to the inventive subject matter.

Thus, according to one example embodiment illustrated in FIG. 4, there is provided a method and corresponding computer program for generating and using a precision profile for a laboratory analyzer in particular, and scientific measurement equipment in general, including:

1. Analyze a series of biological (or non-biological) samples for one or more patients using an analyzer to produce corresponding test results (410).
2. Use the test results to generate a precision profile for serial patient data from the analyzer (420). The precision profile may comprise, for example, a graph that may demonstrate three different zones: 1) increased imprecision for quality control determinations that are close spaced (implies the discovery of an error condition and rapid reanalysis), such as shown in FIGS. 1-2 as the ellipse labeled "higher error prevalence"; 2) the usual imprecision, such as shown in FIGS. 1-2 as the ellipse labeled "standard SD"; and 3) a zone of increased imprecision which indicates either a need for a quality control analysis or re-calibration, such as shown in FIGS. 1-2 as the elliupse labeled "requires QC monitoring after 12 h" and "requires QC monitoring after 16 h," respectively.
3. Perform any of the actions set forth above for quality control or patient data precision in response to information obtained from the precision profile (430).
4. Optionally use the analyzer to analyze further biological samples to produce further corresponding test results (440).

Figure 5:
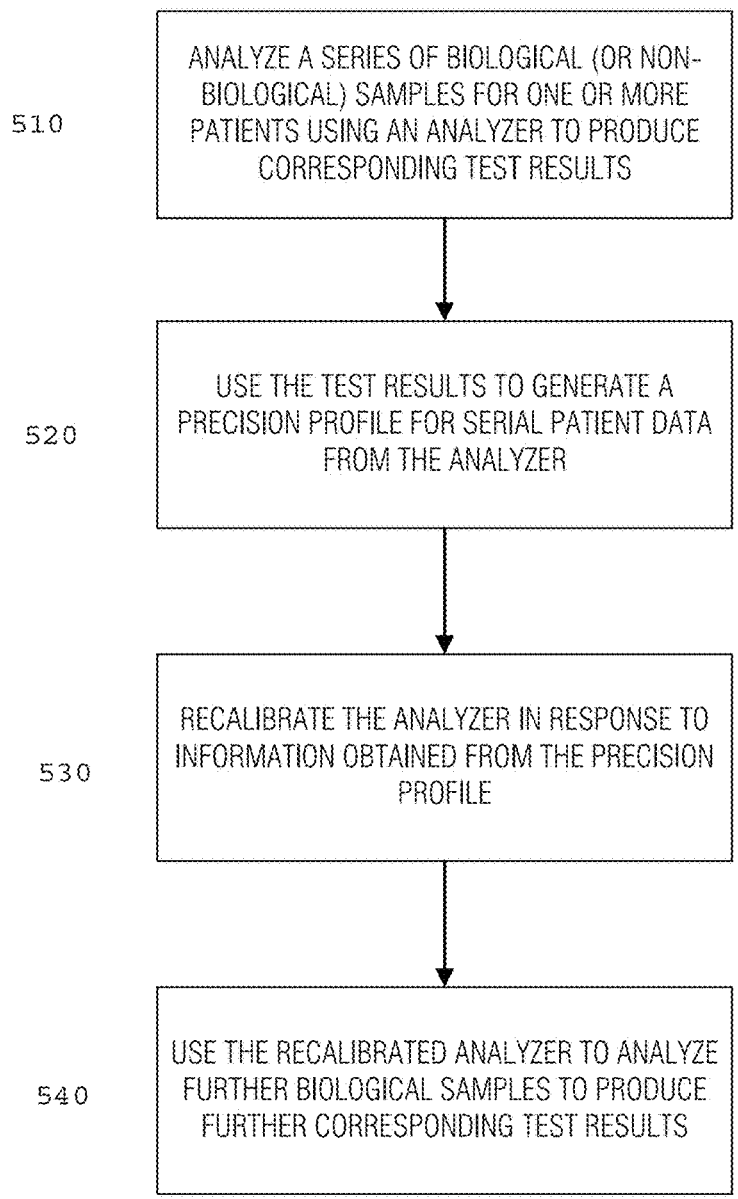

Thus, according to one example embodiment illustrated in FIG. 5, there is provided a method and corresponding computer program for calibrating a laboratory analyzer in particular, and scientific measurement equipment in general, including:

1. Analyze a series of biological (or non-biological) samples for one or more patients using an analyzer to produce corresponding test results (510).
2. Use the test results to generate a precision profile for serial patient data from the analyzer (520). The precision profile may comprise, for example, a graph that may demonstrate three different zones: 1) increased imprecision for quality control determinations that are close spaced (implies the discovery of an error condition and rapid reanalysis), 2) the usual imprecision and 3) a zone of increased imprecision which indicates either a need for a quality control analysis or re-calibration.
3. Re-calibrate the analyzer in response to information obtained from the precision profile (530).
4. Use the recalibrated analyzer to analyze further biological samples to produce further corresponding test results (540).

Figure 6:
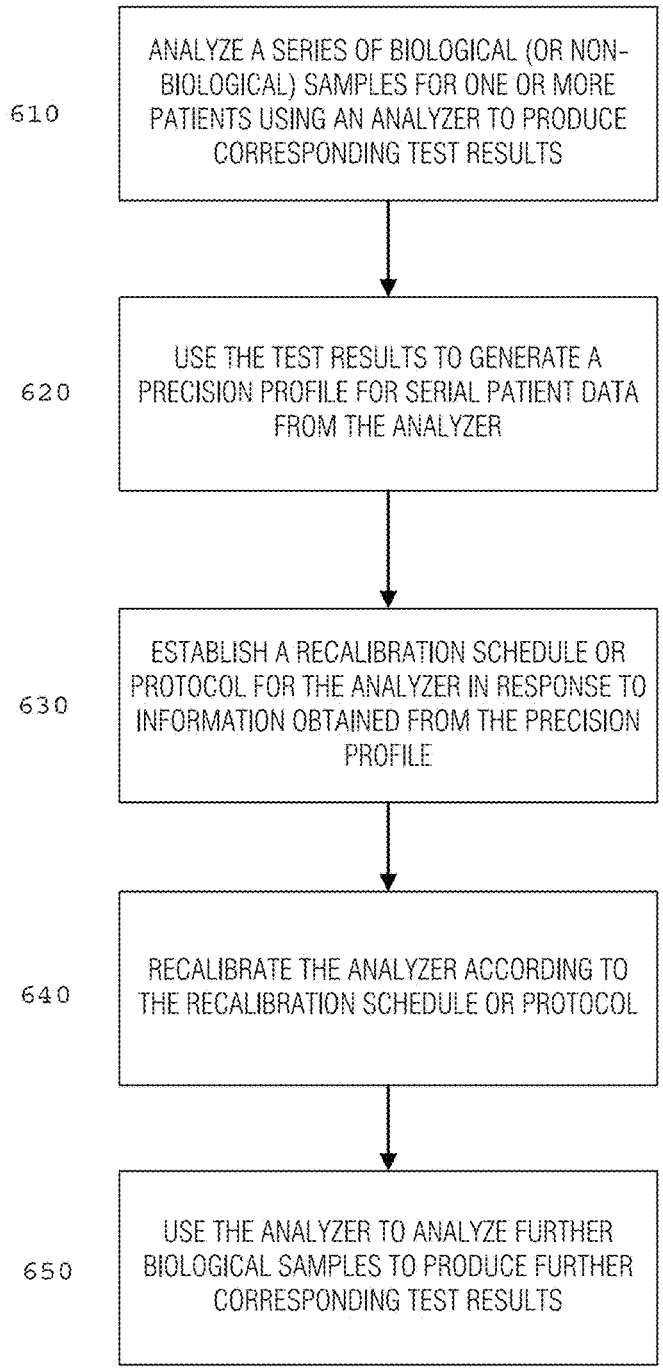

According to another example embodiment illustrated in FIG. 6, there is provided a method and corresponding computer program for establishing a calibration schedule or protocol for a laboratory analyzer in particular, and scientific measurement equipment in general, including:

1. Analyze a series of biological (or non-biological) samples for one or more patients using an analyzer to produce corresponding test results (610).
2. Use the test results to generate a precision profile for serial patient data from the analyzer (620). The precision profile may comprise, for example, a graph that may demonstrate three different zones: 1) increased imprecision for quality control determinations that are close spaced (implies the discovery of an error condition and rapid reanalysis), 2) the usual imprecision and 3) a zone of increased imprecision which indicates either a need for a quality control analysis or re-calibration.
3. Establishing a recalibration schedule or protocol for the analyzer in response to information obtained from the precision profile (630).
4. Recalibrating the analyzer according to the recalibration schedule or protocol (640).
5. Using the analyzer to analyze further biological samples to produce further corresponding test results (650).

Figure 7:
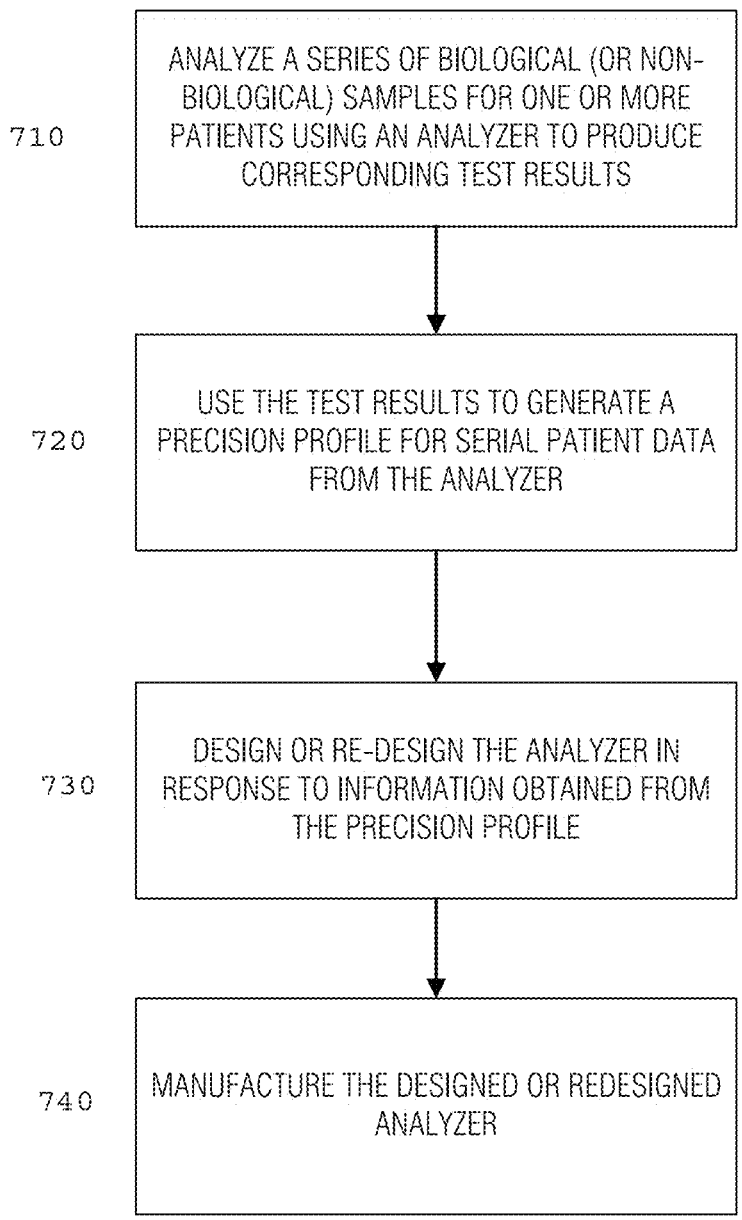

Thus, according to one example embodiment illustrated in FIG. 7, there is provided a method and corresponding computer program for designing or modifying the design of a laboratory analyzer in particular, and scientific measurement equipment in general, including:

1. Analyze a series of biological (or non-biological) samples for one or more patients using an analyzer to produce corresponding test results (710).
2. Use the test results to generate a precision profile for serial patient data from the analyzer (720). The precision profile may comprise, for example, a graph that may demonstrate three different zones: 1) increased imprecision for quality control determinations that are close spaced (implies the discovery of an error condition and rapid reanalysis), 2) the usual imprecision and 3) a zone of increased imprecision which indicates either a need for a quality control analysis or re-calibration.
3. Design or re-design the analyzer in response to information obtained from the precision profile (730).
4. Manufacture the designed or redesigned analyzer (740).

Figure 8:
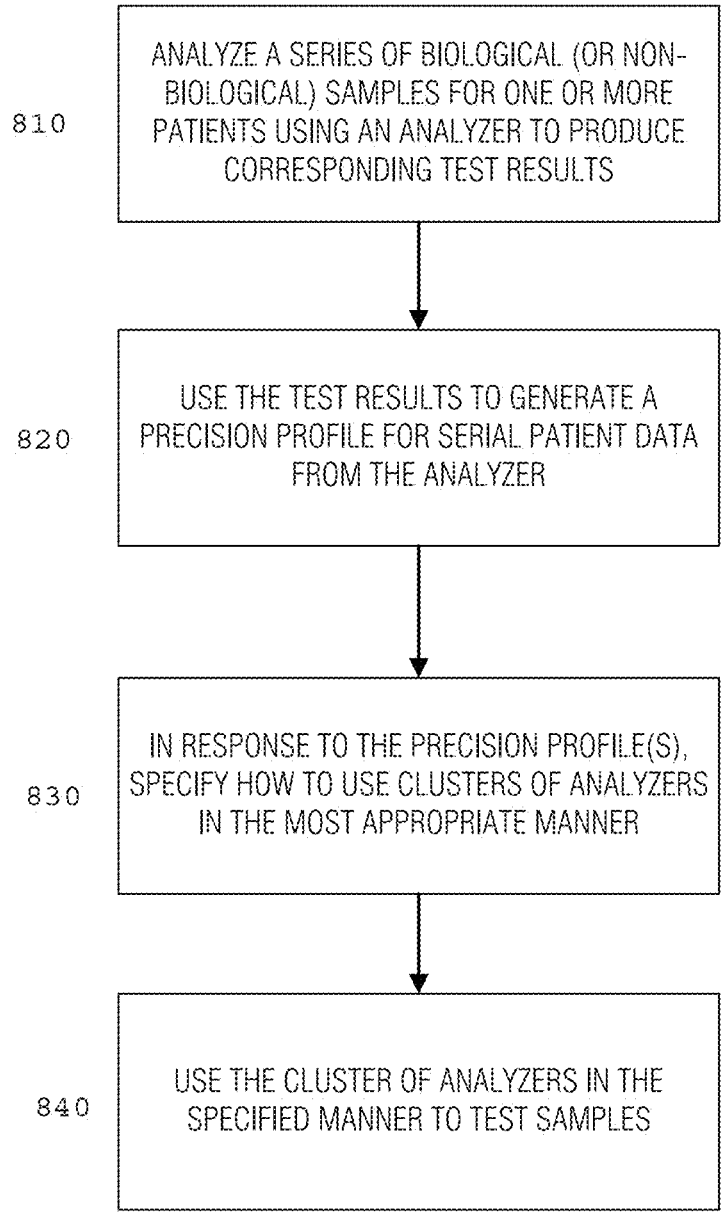

Thus, according to one example embodiment illustrated in FIG. 8, there is provided a method and corresponding computer program for developing a protocol for use of a cluster of laboratory analyzers in particular, and scientific measurement equipment in general, including:

1. Analyze a series of biological (or non-biological) samples for one or more patients using one or more analyzers to produce corresponding test results (810).
2. Use the test results to generate a precision profile for serial patient data from the analyzer(s) (820). The precision profile may comprise, for example, a graph that may demonstrate three different zones: 1) increased imprecision for quality control determinations that are close spaced (implies the discovery of an error condition and rapid reanalysis), 2) the usual imprecision and 3) a zone of increased imprecision which indicates either a need for a quality control analysis or re-calibration.

3. In response to the precision profile or profiles, specifying how to use clusters of analyzers in the most appropriate manner (for example, if a laboratory has two systems, should it be using one system for a week or a month and not run the other or should there be alternation between the two systems, and what would be the most favorable period that each would be run before alternating to the other system) (830).

4. Using the cluster of analyzers in the specified manner to test samples (840).

Figure 9:
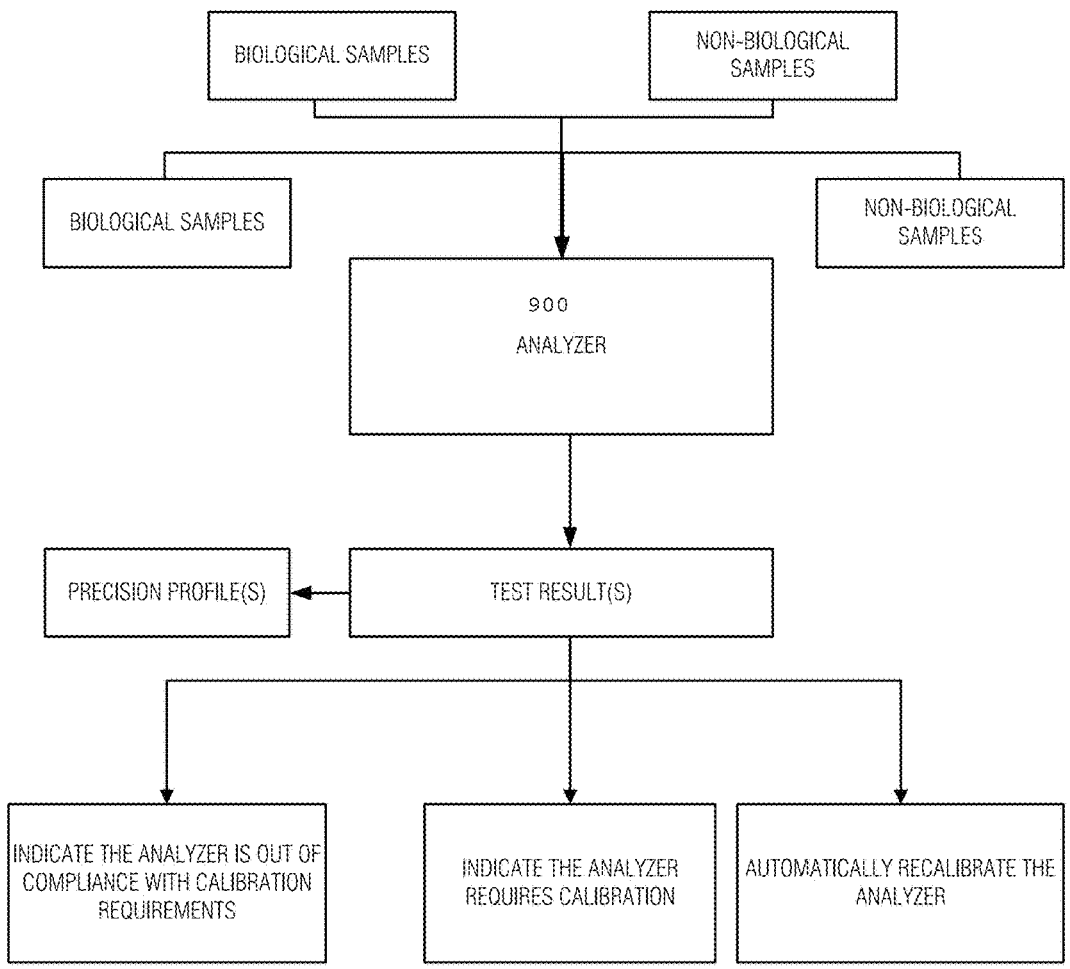
FIG. 9 illustrates a laboratory analyzer.

According to one example embodiment, the computer programs that are used to implement all or any part of the processes described in FIGS. 4 through 8 may be executed on the computer system 1000 illustrated in FIG. 10, or executed on a computing system in analyzer 900 of FIG. 9.

Thus, according to one example embodiment illustrated in FIG. 9, there is provided a laboratory analyzer 900 that is capable of:

1. Analyzing a series of biological (or non-biological) samples for one or more patients using one or more analyzers to produce corresponding test results.
2. Analyzing the test results according to a computer process that is capable of producing all or a portion of a precision profile for serial patient data from the analyzer, and in response to the analysis of the test results automatically performing any one or more of the following:
   a. Indicating the analyzer is out of compliance with calibration requirements;
   b. Indicating the analyzer requires recalibration;
   c. Automatically recalibrating the analyzer.

Referring now to FIG. 10, there is illustrated a computer system 1000 that may be used to execute the computer programs described above with respect to FIG. 4 through 8, and can be used to generate the visual graphs illustrated in FIGS. 1 to 3. In addition, in one example embodiment, the analyzer 900 includes computer system 100 and one or more computer programs stored in its memories or storage unit to perform laboratory analytics, or execute the computer programs described herein to provide calibration.

More particularly, FIG. 10 is a block diagram of a machine in the form of a computing device within which a set of instructions, for causing the machine to perform any one or more of the methodologies discussed herein, may be executed. In alternative embodiments, the machine operates as a standalone device or may be connected (e.g., networked) to other machines. In a networked deployment, the machine may operate in the capacity of a server or a client machine in server-client network environments, or as a peer machine in peer-to-peer (or distributed) network environments. The machine may be a personal computer (PC), a tablet PC, a set-top box (STB), a Personal Digital Assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1000 includes a processor 1002 (e.g., a central processing unit (CPU), a graphics processing unit (GPU) or both), a main memory 1001 and a static memory 1006, which communicate with each other via a bus 1508. The computer system 1500 may further include a display unit 1010, an alphanumeric input device 1017 (e.g., a keyboard), and a user interface (UI) navigation device 1011 (e.g., a mouse). In one embodiment, the display, input device and cursor control device are a touch screen display. The computer system 1000 may additionally include a storage device (e.g., drive unit 1016), a signal generation device 1018 (e.g., a speaker), a network interface device 1020, and one or more sensors 1021, such as a global positioning system sensor, compass, accelerometer, or other sensor.

The drive unit 1016 includes a machine-readable medium 1022 on which is stored one or more sets of instructions and data structures (e.g., software 1023) embodying or utilized by any one or more of the methodologies or functions described herein. The software 1023 may also reside, completely or at least partially, within the main memory 1001 and/or within the processor 1002 during execution thereof by the computer system 1000, the main memory 1001 and the processor 1002 also constituting machine-readable media.

While the machine-readable medium 1022 is illustrated in an example embodiment to be a single medium, the term "machine-readable medium" may include a single medium or multiple media (e.g., a centralized or distributed database, and/or associated caches and servers) that store the one or more instructions. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., EPROM, EEPROM, and flash memory devices; magnetic disks such as internal hard disks and removable disks; magneto-optical disks; and CD-ROM and DVD-ROM disks.

Recently, the Royal Alexandra Hospital, a large tertiary and quaternary level Edmonton, Alberta hospital replaced its 250 and 950 Vitros chemistry analyzers with two Beckman DxC 800 systems. During the conversion to the new analyzers, laboratory staff observed that the number of outliers increased relative to that previously. We have devised a data-mining statistic (within-patient imprecision regressed to zerotime between specimens) that summarizes the average short term analytic imprecision (sa) and minimized biologic patient variation (sb). This statistic can summarize the analytic imprecision over many reagent lots and calibrations.

We analyzed two 12 month periods of Vitros data and a single 10 month period of Beckman data. For chloride, $CO_2$, creatinine, potassium and sodium, we tabulated the measurements of paired intra-patient samples drawn within 24 hours of each other. After outlier removal, we calculated the standard deviations of duplicates (SDD) of the intra-patient pairs grouped in two-hour intervals: 0-2 hours, 2-4 hours, 4-6 hours, ¼ 20-22 hours and 22-24 hours. The SDDs were then regressed against the time intervals of 2 to 14 hours; extrapolation to zero time (y-intercept) represents the average variation $(sa^2+sb^2)1/2$. For each test, sa was calculated from the product of the short term within run experimental coefficient of variation (CV) and the control concentration. sb was calculated from sa and y0. CVb was determined by dividing sb by the average patient concentration. The uncertainty of CVb was derived from the standard error of the y-intercept; the relative error was obtained by dividing by the y-intercept.

sVitros was calculated using sb from Westgard.com. The increased imprecision due to using the Beckmans was derived from the square root of the differences of the squares of the SDD intercepts. The data mining tool, the within-patient imprecision regressed to zero-time between specimens, appears to be a powerful tool for evaluating imprecision.

Method stability and analytical imprecision are two of the most important criteria for instrument selection. We have devised a data-mining statistic (within-patient imprecision regressed to zero-time between specimens [WPI]) that summarizes the average short term analytic imprecision (sa) and minimizes biologic patient variation (sb). Unlike the short term analytic imprecision that is derived from quality control data, this statistic can summarize the analytic imprecision over many reagent lots and calibrations. Acute care hospitals and intensive care units provide adequate data to generate this imprecision statistic. This statistic can be used to compare the analytic performance of different analyzers operating in similar patient care environments.

This data-mining statistic is derived from the y intercept of the regression line of the standard deviations of intra-patient differences graphed against the time intervals between sampling. This statistic can summarize the analytic imprecision over many reagent lots and calibrations.

After outlier removal, we calculated the standard deviations of duplicates (SDD) of the intra-patient pairs grouped in two-hour intervals: 0-2 hours, 2-4 hours, 4-6 hours, ¼ 20-22 hours and 22-24 hours. The WPI were obtained by regressing the SDDs against the time intervals of 2 to 14 hours; extrapolation to zero time (yintercept) represents the WPI (sa2+sb2)1/2.

Two groups of data were excluded from analysis: (1) Highly abnormal results which render the WPI calculation inaccurate. We generated frequency histograms of the patient data and in combination with the knowledge of reference intervals, we truncated significantly outlying data. (2) Results repeated within 2 hr. Reasons for serial testing within 2 hr include the investigation of a very morbid physiologic states, confirmation of very abnormal laboratory results and determining the response to an extreme therapy.

The software 1023 may further be transmitted or received over a communications network 1026 using a transmission medium via the network interface device 1020 utilizing any one of a number of well-known transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., Wi-Fi® and WiMax® networks). The term "transmission medium" shall be taken to include any intangible medium that is capable of storing, encoding or carrying instructions for execution by the machine, and includes digital or analog communications signals or other intangible medium to facilitate communication of such software.

Recently, the Royal Alexandra Hospital, a large tertiary and quaternary level Edmonton, Alberta hospital replaced its 250 and 950 Vitros chemistry analyzers with two Beckman DxC 800 systems. During the conversion to the new analyzers, laboratory staff observed that the number of outliers increased relative to that previously. We have devised a data-mining statistic (within-patient imprecision regressed to zerotime between specimens) that summarizes the average short term analytic imprecision (sa) and minimized biologic patient variation (sb). This statistic can summarize the analytic imprecision over many reagent lots and calibrations.

We analyzed two 12 month periods of Vitros data and a single 10 month period of Beckman data. For chloride, CO2, creatinine, potassium and sodium, we tabulated the measurements of paired intra-patient samples drawn within 24 hours of each other. After outlier removal, we calculated the standard deviations of duplicates (SDD) of the intra-patient pairs grouped in two-hour intervals: 0-2 hours, 2-4 hours, 4-6 hours, ¼ 20-22 hours and 22-24 hours. The SDDs were then regressed against the time intervals of 2 to 14 hours; extrapolation to zero time (y-intercept) represents the average variation (sa2+sb2)1/2. For each test, sa was calculated from the product of the short term within run experimental coefficient of variation (CV) and the control concentration. sb was calculated from sa and y0. CVb was determined by dividing sb by the average patient concentration. The uncertainty of CVb was derived from the standard error of the y-intercept; the relative error was obtained by dividing by the y-intercept.

sVitros was calculated using sb from Westgard.com. The increased imprecision due to using the Beckmans was derived from the square root of the differences of the squares of the SDD intercepts. The data mining tool, the within-patient imprecision regressed to zero-time between specimens, appears to be a powerful tool for evaluating imprecision.

Method stability and analytical imprecision are two of the most important criteria for instrument selection. We have devised a data-mining statistic (within-patient imprecision regressed to zero-time between specimens [WPI]) that summarizes the average short term analytic imprecision (sa) and minimizes biologic patient variation (sb). Unlike the short term analytic imprecision that is derived from quality control data, this statistic can summarize the analytic imprecision over many reagent lots and calibrations. Acute care hospitals and intensive care units provide adequate data to generate this imprecision statistic. This statistic can be used to compare the analytic performance of different analyzers operating in similar patient care environments.

This data-mining statistic is derived from the y intercept of the regression line of the standard deviations of intra-patient differences graphed against the time intervals between sampling. This statistic can summarize the analytic imprecision over many reagent lots and calibrations.

After outlier removal, we calculated the standard deviations of duplicates (SDD) of the intra-patient pairs grouped in two-hour intervals: 0-2 hours, 2-4 hours, 4-6 hours, ¼ 20-22 hours and 22-24 hours. The WPI were obtained by regressing the SDDs against the time intervals of 2 to 14 hours; extrapolation to zero time (yintercept) represents the WPI (sa2+sb2)1/2.

Two groups of data were excluded from analysis: (1) Highly abnormal results which render the WPI calculation inaccurate. We generated frequency histograms of the patient data and in combination with the knowledge of reference intervals, we truncated significantly outlying data. (2) Results repeated within 2 hr. Reasons for serial testing within 2 hr include the investigation of a very morbid physiologic states, confirmation of very abnormal laboratory results and determining the response to an extreme therapy.

What is claimed is:

1. A method of calibrating laboratory analyzer equipment comprising:
   using the laboratory analyzer equipment to generate sample results, the sample results including measurements of a single analyte from multiple persons;
   determining a within-patient variation including:
      determining average intra-patient variations of the sample results provided by the laboratory analyzer over a period of time;
      determining an axis-intercept using a regression of the average intra-patient variations versus time between the sample results;
      determining the within-patient variation as a function of the axis-intercept; and
   calibrating the laboratory analyzer equipment as a function of the determined within-patient variation; and
   using the calibrated laboratory analyzer equipment to generate further sample results of the single analyte.

2. The method of claim 1, further comprising obtaining the sample results by data-mining previous results provided by the laboratory analyzer.

3. The method of claim 2, wherein obtaining sample results includes obtaining sample results that were only provided for clinical care of the multiple persons.

4. The method of claim 1, further comprising grouping the sample results by a time interval in which the sample results were provided, and wherein calculating the average intra-patient variation includes calculating the average intra-patient variation for each time interval.

5. The method of claim 1, further comprising removing out-lying sample results before calculating the average intra-patient variation.

6. The method of claim 5, wherein removing out-lying sample results includes removing out-lying sample results as a function of a frequency histogram and removing sample results from a repeated measurement made within a specific time period.

7. The method of claim 5, wherein removing out-lying sample results includes removing sample results from a repeated measurement made within two hours.

8. The method of claim 1, wherein calculating the within-patient variation includes using the formula:

within-patient variation=$((\text{axis-intercept})^2-(\text{analytic variation})^2)^{1/2}$.

9. The method of claim 8, further comprising calculating the analytic variation as a function of a chemical concentration and an experimental coefficient of variation.

10. A system comprising:
    laboratory analyzer equipment that performs measurements on biological samples, including one or more analytes of multiple persons, to generate sample results;
    a memory storing the sample results obtained from measuring the biological samples using the laboratory analyzer equipment;
    a display;
    a processor communicatively coupled to the memory, the display, and the laboratory analyzer equipment;
    the memory storing instructions, which when executed by the processor, cause the processor to:
       calculate a within-patient variation including:
          determining average intra-patient variations of the sample results obtained from the memory;
          determining an axis-intercept using a regression of the average intra-patient variations versus time between the sample results;
          determining the within-patient variation as a function of the axis-intercept; and
       determine calibration information as a function of the within-patient variation; and
       calibrate the laboratory analyzer equipment based on the calibration information; and
       wherein the laboratory analyzer equipment performs further measurements, after calibration, on the biological samples to generate calibrated sample results.

11. The system of claim 10, wherein the memory further stores instructions, which when executed by the processor, cause the processor to perform operations comprising obtaining the sample results by data-mining previous results provided by the laboratory analyzer equipment.

12. The system of claim 11, wherein the sample results only sample results provided for clinical care of the multiple persons.

13. The system of claim 12, wherein the memory further stores instructions, which when executed by the processor, cause the processor to group the sample results into groups of time intervals, and wherein the instructions for determining the average intra-patient variation include instructions for determining the average intra-patient variation for each time interval.

14. The system of claim 10, wherein the memory further stores instructions, which when executed by the processor, cause the processor to perform operations comprising removing out-lying sample results before calculating the average intra-patient variation.

15. The system of claim 14, wherein the instructions for removing out-lying sample results include instructions for removing out-lying sample results as a function of a frequency histogram and removing sample results from repeated measurements made within a specific time period of each other.

16. The system of claim 15, wherein the instructions for removing out-lying sample results include instructions for removing sample results from a repeated measurement made within two hours.

17. The system of claim 10, wherein the instructions for calculating the within-patient variation include instruction for calculating the within-patient variation using the formula:

within-patient variation=$((\text{axis-intercept})^2-(\text{analytic variation})^2)^{1/2}$, 18. The system of claim 17, wherein the memory further stores instructions, which when executed by the processor, cause the machine to perform operations comprising calculating the analytic variation as a function of a chemical concentration and an experimental coefficient of variation.

19. The system of claim 10, the memory further stores instructions, which when executed by the processor, cause the processor to determine a precision profile of the user and send the precision profile to the display, wherein the precision profile includes a graph of the average intra-patient variations of the sample results provided by the laboratory analyzer equipment over a period of time.

* * * * *